(12) United States Patent
Viola et al.

(10) Patent No.: US 6,554,779 B2
(45) Date of Patent: Apr. 29, 2003

(54) BIOPSY INSTRUMENT DRIVER APPARATUS

(75) Inventors: Frank J. Viola, Sandy Hook, CT (US); James Dale, Nashua, NH (US); Arthur C. Stickney, Deering, NH (US)

(73) Assignee: United States Surgical Corporation, Norwalk, CT (US)

( * ) Notice: Subject to any disclaimer, the term of this patent is extended or adjusted under 35 U.S.C. 154(b) by 74 days.

(21) Appl. No.: 09/785,736

(22) Filed: Feb. 16, 2001

(65) Prior Publication Data

US 2001/0011156 A1 Aug. 2, 2001

Related U.S. Application Data

(63) Continuation of application No. 09/252,548, filed on Feb. 19, 1999, now Pat. No. 6,193,673.
(60) Provisional application No. 60/078,748, filed on Feb. 20, 1998.

(51) Int. Cl.$^7$ ............................................... A61B 10/00
(52) U.S. Cl. ......................................................... 600/568
(58) Field of Search ................................ 600/562–568; 604/164.01, 164.11, 264

(56) References Cited

U.S. PATENT DOCUMENTS

| | | |
|---|---|---|
| 737,293 A | 8/1903 | Summerfeldt |
| 1,585,934 A | 5/1926 | Muir |
| 1,663,761 A | 3/1928 | Johnson |
| 1,867,624 A | 7/1932 | Hoffman |
| 2,729,210 A | 1/1956 | Spencer |
| 3,173,414 A | 3/1965 | Guillant |
| 3,400,708 A | 9/1968 | Scheidt |
| 3,477,423 A | 11/1969 | Griffith |
| 3,561,429 A | 2/1971 | Jewett et al. |

(List continued on next page.)

FOREIGN PATENT DOCUMENTS

| | | |
|---|---|---|
| DE | 935 625 | 11/1955 |
| DE | 1 817 555 | 1/1971 |
| DE | 27 19 959 A1 | 11/1978 |
| DE | 159 394 | 3/1983 |
| DE | 42 16 694 A1 | 12/1992 |
| EP | 0 010 321 A1 | 4/1980 |
| EP | 0 019 104 | 11/1980 |
| EP | 0 207 726 A2 | 1/1987 |

(List continued on next page.)

OTHER PUBLICATIONS

Automatic Soft Tissue Biopsy System, (ASAP™) Operational Guidelines, Microvasive Boston Scientific Corp., (2 pgs.).

When it Comes to Core Samples, I Demand Accuracy and Consistency for all my Patients, The Bard Biopty Biopsy System, Bard® Radiology, (4 pgs.).

Nucleotome® System Automated Percutaneous Lumbar Disectomy™, Surgical Dynamics®, (3 pgs.).

(List continued on next page.)

Primary Examiner—Max F. Hindenburg
Assistant Examiner—Pamela L Wingood

(57) ABSTRACT

A driver apparatus is provided for use with a biopsy instrument, the driver apparatus including a housing and an insertion mechanism including a carriage movably associated with the housing and adapted to support the biopsy instrument to affect longitudinal movement of at least a portion of the biopsy instrument. A linear motion control mechanism is also included that is adapted to move a tissue cutting element of the biopsy instrument from a first position to a second position relative to a tissue receiving portion of the biopsy instrument. Further, a tissue retract mechanism is included which facilitates removal of a tissue specimen from the biopsy instrument without removing the entire biopsy instrument from a surgical site.

9 Claims, 12 Drawing Sheets

U.S. PATENT DOCUMENTS

| | | |
|---|---|---|
| 3,590,808 A | 7/1971 | Muller |
| 3,606,878 A | 9/1971 | Kellogg, Jr. |
| 3,732,858 A | 5/1973 | Banko |
| 3,734,099 A | 5/1973 | Bender et al. |
| 3,844,272 A | 10/1974 | Banko |
| 3,929,123 A | 12/1975 | Jamshidi |
| 3,989,033 A | 11/1976 | Halpern |
| 3,995,619 A | 12/1976 | Glatzer |
| 4,099,518 A | 7/1978 | Baylis et al. |
| 4,200,106 A | 4/1980 | Douvas et al. |
| 4,203,444 A | 5/1980 | Bonnell et al. |
| 4,210,146 A | 7/1980 | Banko |
| 4,340,066 A | 7/1982 | Shah |
| 4,396,021 A | 8/1983 | Baumgartner |
| 4,445,517 A | 5/1984 | Feild |
| 4,600,014 A | 7/1986 | Beraha |
| 4,644,951 A | 2/1987 | Bays |
| 4,651,753 A | 3/1987 | Lifton |
| 4,660,267 A | 4/1987 | Wheeler |
| 4,662,869 A | 5/1987 | Wright |
| 4,674,502 A | 6/1987 | Imonti |
| 4,681,123 A | 7/1987 | Valtchev |
| 4,699,154 A | 10/1987 | Lindgren |
| 4,702,260 A | 10/1987 | Wang |
| 4,702,261 A | 10/1987 | Cornell et al. |
| 4,708,147 A | 11/1987 | Haaga |
| 4,711,250 A | 12/1987 | Gilbaugh, Jr. et al. |
| 4,733,671 A | 3/1988 | Mehl |
| 4,735,215 A | 4/1988 | Goto et al. |
| 4,776,346 A | 10/1988 | Beraha et al. |
| 4,781,202 A | 11/1988 | Janese |
| 4,790,329 A | 12/1988 | Simon |
| 4,799,494 A | 1/1989 | Wang |
| 4,838,280 A | 6/1989 | Haaga |
| 4,844,088 A | 7/1989 | Kambin |
| 4,874,375 A | 10/1989 | Ellison |
| 4,881,551 A | 11/1989 | Taylor |
| 4,907,598 A | 3/1990 | Bauer |
| 4,907,599 A | 3/1990 | Taylor |
| 4,917,100 A | 4/1990 | Nottke |
| 4,924,878 A | 5/1990 | Nottke |
| 4,936,835 A | 6/1990 | Haaga |
| RE33,258 E | 7/1990 | Onik et al. |
| 4,940,061 A | 7/1990 | Terwilliger et al. |
| 4,944,308 A | 7/1990 | Akerfeldt |
| 4,953,558 A | 9/1990 | Akerfeldt |
| 4,958,625 A | 9/1990 | Bates et al. |
| 4,976,269 A | 12/1990 | Mehl |
| 4,989,614 A | 2/1991 | Dejter, Jr. et al. |
| 4,991,592 A | 2/1991 | Christ |
| 5,031,634 A | 7/1991 | Simon |
| 5,036,860 A | 8/1991 | Leigh et al. |
| 5,047,008 A | 9/1991 | de Juan, Jr. et al. |
| 5,048,538 A | 9/1991 | Terwilliger |
| 5,080,655 A | 1/1992 | Haaga |
| 5,106,364 A | 4/1992 | Hayafuji et al. |
| 5,121,751 A | 6/1992 | Panalletta |
| 5,127,419 A | 7/1992 | Kaldany |
| RE34,056 E | 9/1992 | Lindgren et al. |
| 5,146,921 A | 9/1992 | Terwilliger et al. |
| 5,183,052 A | 2/1993 | Terwilliger et al. |
| 5,183,054 A | 2/1993 | Burkholder et al. |
| 5,188,118 A | 2/1993 | Terwilliger |
| 5,195,533 A | 3/1993 | Chin et al. |
| 5,195,988 A | 3/1993 | Haaga |
| 5,199,441 A | 4/1993 | Hogle |
| 5,213,110 A | 5/1993 | Kedem et al. |
| 5,220,926 A | 6/1993 | Jones |
| 5,224,488 A | 7/1993 | Neuffer |
| 5,226,909 A | 7/1993 | Evans et al. |
| 5,226,910 A | 7/1993 | Kajiyama et al. |
| 5,243,994 A | 9/1993 | Ranalletta |
| 5,249,582 A | 10/1993 | Taylor |
| 5,249,583 A | 10/1993 | Mallaby |
| 5,254,105 A | 10/1993 | Haaga |
| 5,273,051 A | 12/1993 | Wilk |
| 5,282,476 A | 2/1994 | Terwilliger |
| 5,284,156 A | 2/1994 | Schramm et al. |
| 5,285,795 A | 2/1994 | Ryan et al. |
| 5,290,303 A | 3/1994 | Pingleton et al. |
| 5,301,684 A | 4/1994 | Ogirala |
| 5,313,958 A | 5/1994 | Bauer |
| 5,316,013 A | 5/1994 | Striebel, II et al. |
| 5,320,110 A | 6/1994 | Wang |
| 5,368,045 A | 11/1994 | Clement et al. |
| 5,405,321 A | 4/1995 | Reeves |
| 5,415,182 A | 5/1995 | Chin et al. |
| 5,425,376 A | 6/1995 | Banys et al. |
| 5,458,112 A | 10/1995 | Weaver |
| 5,476,101 A | 12/1995 | Schramm et al. |
| 5,477,862 A | 12/1995 | Haaga |
| 5,492,130 A | 2/1996 | Chiou |
| 5,505,211 A | 4/1996 | Ohto et al. |
| 5,511,556 A | 4/1996 | DeSantis |
| 5,526,822 A | 6/1996 | Burbank et al. |
| 5,535,755 A | 7/1996 | Heske |
| 5,546,957 A | 8/1996 | Heske |
| 5,560,373 A | 10/1996 | De Santis |
| 5,649,547 A | 7/1997 | Richart et al. |
| 5,655,542 A | 8/1997 | Weilandt |
| 5,752,923 A | 5/1998 | Terwilliger |
| 5,769,086 A | 6/1998 | Ritchart et al. |
| 5,775,333 A | 7/1998 | Burbank et al. |
| 5,779,647 A | 7/1998 | Chau et al. |
| 5,817,033 A | 10/1998 | DeSantis et al. |
| 6,077,230 A | 6/2000 | Gregiore et al. |

FOREIGN PATENT DOCUMENTS

| | | |
|---|---|---|
| EP | 0 238 461 A1 | 9/1987 |
| EP | 0 378 692 | 7/1990 |
| EP | 0 442 851 A1 | 8/1991 |
| EP | 0 536 888 A1 | 4/1993 |
| EP | 0 561 732 A1 | 9/1993 |
| FR | 1 161 400 | 8/1958 |
| FR | 1 267 960 | 6/1960 |
| FR | 2 332 743 | 6/1977 |
| FR | 2 654 609 | 5/1991 |
| GB | 1 255 330 | 12/1971 |
| GB | 1 393 068 | 5/1975 |
| GB | 2 237 992 A | 5/1991 |
| SU | 400319 | 2/1974 |
| SU | 520 976 | 7/1976 |
| SU | 648 219 | 2/1979 |
| SU | 707 576 | 1/1980 |
| SU | 0728 852 | 5/1980 |
| SU | 1192 795 A | 11/1985 |
| WO | WO 91/01112 | 2/1991 |
| WO | WO 92/00040 | 1/1992 |
| WO | WO 92/19159 | 11/1992 |
| WO | WO 93/12707 | 7/1993 |
| WO | WO 93/14707 | 8/1993 |
| WO | WO 83/03343 | 10/1993 |
| WO | WO 93/20753 | 10/1993 |
| WO | WO 94/08512 | 4/1994 |
| WO | WO 94/26172 | 11/1994 |
| WO | WO 88/07839 | 10/1998 |

OTHER PUBLICATIONS

Introducing the Singular Technology for Multi–Core Microcalcification Sampling, *Biopsys Medical Inc.*, (2 pgs.).

Mammotome Multi–Probe, Probe and Motorized Driver, Instructions for Use, *Biopsys Medical Inc.*, (3 pgs.).

PCT International Search Report—PCT/US98/19422.

Stereotactic Breast Biopsy with a Biopsy Gun, Parker, MD et al., pp. 741–747, Sep. 1990.

Stereotactic Percutaneous Breast Core Biopsy Technical Adaptation and Initial Experience, Lovin, MD et al., pps. 135–143, 1990.

Selective use of Image–Guided Large–Core Needle Biopsy of the Breast: Accuracy and Cost–Effectiveness, Doyle et al., pps. 281–284, Aug. 1995.

Breast Biopsy: A Comparative Study of Stereotaxially Guided Core and Excisional Techniques, Gisvold et al., pps. 815–820, Apr., 1994.

Stereotactic Core Needle Biopsy of Mammographic Breast Lesions as a Viable Alternative to Surgical Biopsy, Mikhail, MD et al., pps. 363–367, 1994.

BIOPSY INSTRUMENT DRIVER APPARATUS

CROSS REFERENCE TO RELATED APPLICATIONS

This application is a continuation application of U.S. application Ser. No. 09/252,548 filed Feb. 19, 1999 now U.S. Pat. No. 6,193,673 which claims priority to U.S. Provisional Application Serial No. 60/078,748 filed Feb. 20, 1998 entitled BIOPSY INSTRUMENT DRIVER APPARATUS, the entire contents of which are incorporated by reference.

TECHNICAL FIELD

This disclosure relates to an apparatus and method for the biopsy of tissue specimens and, more particularly, to a driver apparatus for biopsy instruments.

BACKGROUND OF RELATED ART

It is often necessary to sample tissue in order to diagnose and treat patients suspected of having cancerous tumors, pre-malignant conditions and other diseases or disorders. Typically, in the case of suspected cancerous tissue, when the physician establishes by means of procedures such as palpation, x-ray or ultrasound imaging that suspicious conditions exist, a biopsy is performed to determine whether the cells are cancerous. Biopsy may be done by an open or percutaneous technique. Open biopsy removes the entire mass (excisional biopsy) or a part of the mass (incisional biopsy). Percutaneous biopsy on the other hand is usually done with a needle-like instrument and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment tissue is obtained for histologic examination which may be done via frozen section or paraffin section. In more recent developments percutaneous techniques have been used to remove the entire mass during the initial procedure.

Intact tissue from the organ or lesion is preferred by medical personnel in order to arrive at a definitive diagnosis regarding the patient's condition. In most cases only part of the tissue or lesion need be sampled. The portions of tissue extracted must be indicative of the tissue or lesion as a whole. In the past, to obtain adequate tissue from organs or lesions within the body, surgery was performed so as to reliably locate, identify and remove the tissue. With present technology, medical imaging equipment such as stereotactic x-ray, fluoroscopy, computer tomography, ultrasound, nuclear medicine and magnetic resonance imaging, may be used. These technologies make it possible to identify small abnormalities even deep within the body. However, definitive tissue characterization still requires obtaining adequate tissue samples to characterize the histology of the organ or lesion.

The introduction of image guided percutaneous breast biopsies offers alternatives to open surgical breast biopsy. With time, these guidance systems have become more accurate and easier to use. Biopsy guns were introduced for use in conjunction with these guidance systems. Accurate placement of the biopsy guns was important to obtain useful biopsy information because only one small core could be obtained per insertion at any one location. To sample the tissue thoroughly, many separate insertions of the instrument are often required.

Biopsy procedures may benefit from larger tissue samples being taken, for example, tissue samples as large as 10 mm across. Many of the prior art devices required multiple punctures into the breast or organ in order to obtain the necessary samples. This practice is both tedious and time consuming.

One further solution to obtain a larger tissue sample is to utilize a device capable of taking multiple tissue samples with a single insertion of an instrument. An example of such a device is found in U.S. Pat. No. 5,195,533 to Chin et al. which describes a technique for extracting multiple samples with a single insertion of the biopsy device. Generally, such biopsy instruments extract a sample of tissue from a tissue mass by either drawing a tissue sample into a hollow needle via an external vacuum source or by severing and containing a tissue sample within a notch formed on a stylet. Typical of such devices utilizing an external vacuum source are U.S. Pat. No. 5,246,011 issued to Cailouette and U.S. Pat. No. 5,183,052 issued to Terwiliger. Such devices generally contemplate advancing a hollow needle into a tissue mass and applying a vacuum force to draw a sample into the needle and hold the same therein while the tissue is extracted. These devices require an operator to manually perform some of the separate functions involved in extracting tissue samples. These functions, include, for example, translating the needle within a patient, actuating a cutting mechanism, and actuating a vacuum source.

When extracting multiple samples with a single insertion of the biopsy device using suction to either draw in tissue or remove the tissue from the body, it is important that reliable samples are extracted for accurate diagnosis. If the operator is required to frequently manipulate and adjust a device to accommodate the several functions, the reliability and integrity of the sample may be compromised.

Therefore, a continuing need exists for driver apparatus which can reliably introduce biopsy instruments to extract adequate biopsy sample(s) and reduce the number of operations required to be performed by an operator.

SUMMARY

One particular embodiment of the present disclosure provides a surgical biopsy apparatus which includes a driver apparatus for use with a biopsy instrument which includes a plurality of relatively movable elongated members. The driver apparatus includes a housing, an insertion mechanism, a linear control mechanism and a tissue retract mechanism. The driver apparatus may be mounted to an imaging table and may also communicate with a vacuum/controller module.

The insertion mechanism includes a carriage that is movably associated with the housing. The carriage is adapted to support the biopsy instrument to affect longitudinal movement of at least a portion of the biopsy instrument relative to the housing.

The linear motion control mechanism is adapted to move a tissue cutting element of the biopsy instrument from a first position to a second position relative to a tissue receiving portion of the biopsy instrument. The tissue cutting element cuts tissue extending into a tissue receiving portion of the biopsy instrument.

The tissue retract mechanism facilitates removal of a tissue specimen from the biopsy instrument without removing the entire biopsy instrument from a surgical site. The tissue retract mechanism includes a retention member adapted to retain a portion of the biopsy instrument. The tissue retract mechanism further includes a longitudinal guide member which slidably guides the retention member and is disposed relative to the housing in a manner to permit movement of the longitudinal guide member relative to the housing.

In an alternate embodiment of the present disclosure, a surgical biopsy apparatus is provided which includes a driver apparatus for use with a biopsy instrument which includes a tissue receiving portion and a cutting element. The driver apparatus includes a housing, an insertion mechanism and a cutting element controller assembly. The insertion mechanism is adapted to support a biopsy instrument thereon. The insertion mechanism includes a carriage that is movably associated with the housing. The carriage is movable from a retracted position to an advanced position to affect longitudinal movement of the biopsy instrument. The cutting element controller assembly is operatively disposed on the housing. The controller assembly includes a linear motion control mechanism, a motor and an enabling switch.

The linear motion control mechanism is adapted to move a tissue cutting element of the biopsy instrument from a first position to a second position relative to a tissue receiving portion of the biopsy instrument. The tissue cutting element cuts tissue extending into a tissue receiving portion of the biopsy instrument.

The motor is operatively associated with the cutting element when the biopsy instrument is mounted on the biopsy instrument driver apparatus. The motor facilitates movement of the cutting element relative to the tissue receiving portion.

The enabling switch is disposed relative to the linear motion control member and electrically connected to the motor. Movement of the linear motion control member from the second position to the first position causes the switch to activate the motor.

BRIEF DESCRIPTION OF THE DRAWINGS

Various embodiments are described herein with reference to the drawings, wherein.

DETAILED DESCRIPTION OF PREFERRED EMBODIMENTS

Figure 1:
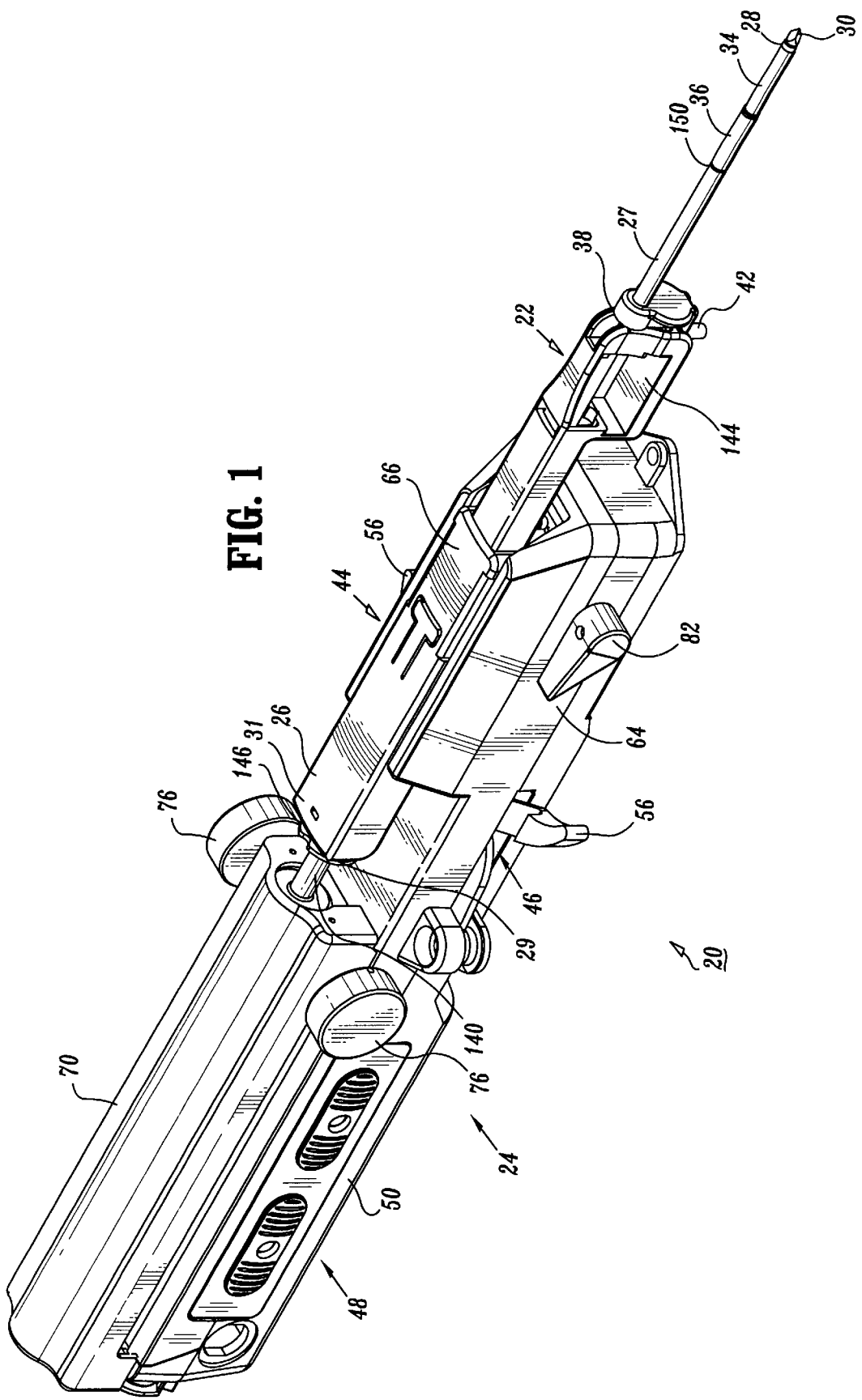
FIG. 1 is a perspective view of one embodiment of a percutaneous biopsy instrument driver apparatus constructed in accordance with the present disclosure.

Referring now in specific detail to the drawings in which like reference numerals identify similar or identical elements throughout the several views, and initially to FIG. 1, one embodiment of an instrument driver biopsy apparatus is shown generally as apparatus 24. Apparatus 24 is adapted to removably retain and operate a biopsy instrument such as biopsy instrument 22. Apparatus 24 may communicate with a vacuum/controller module (not shown), which provides a vacuum source, and is mountable to a medical imaging apparatus (not shown), such as, for example, stereotactic x-ray, fluoroscopy, computer tomography, ultrasound, or other suitable imaging modalities.

Figure 2:
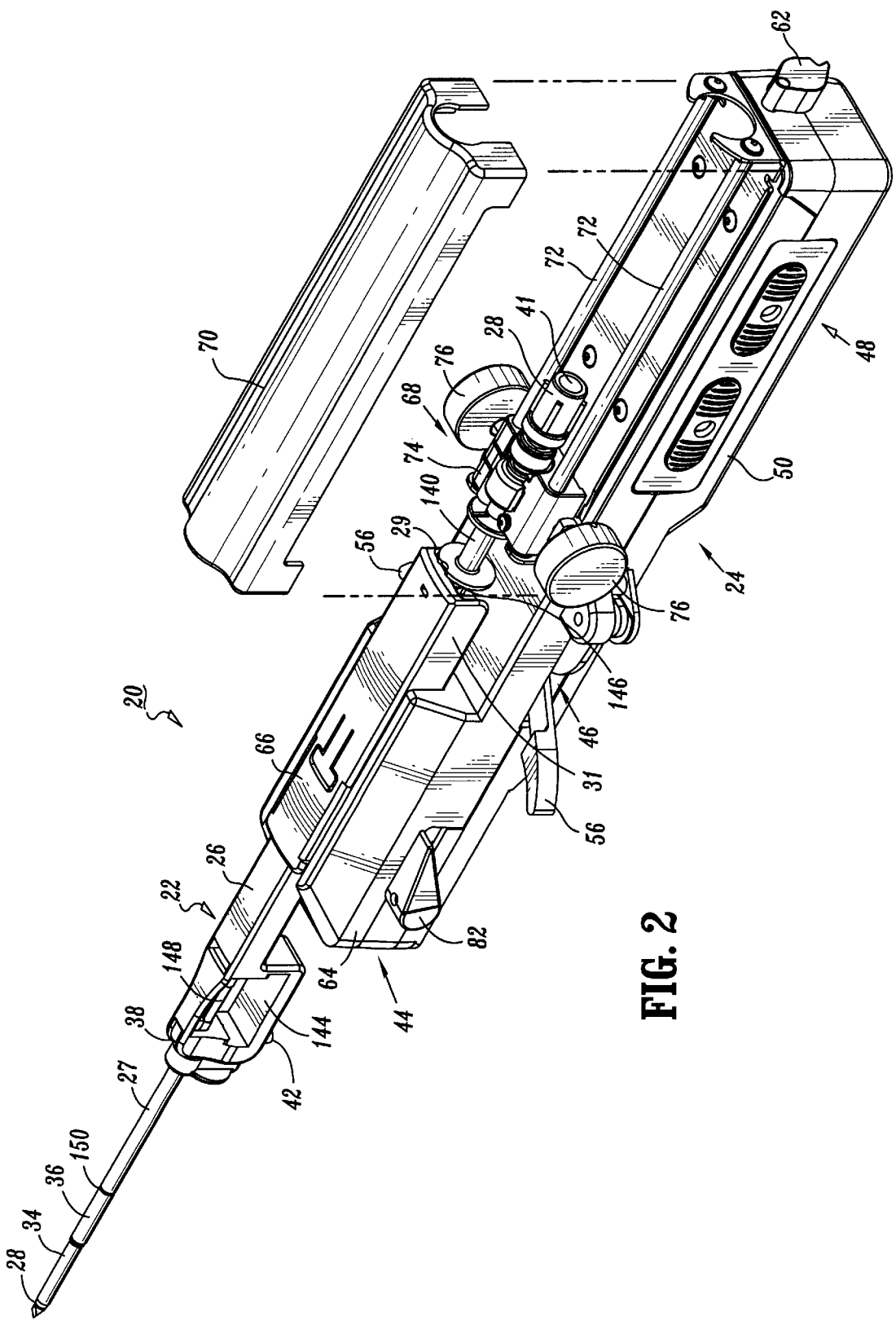
FIG. 2 is a perspective view from a reverse angle perspective to that of FIG. 1 which shows detachably mounting a cover onto the biopsy instrument driver apparatus.
Figure 3:
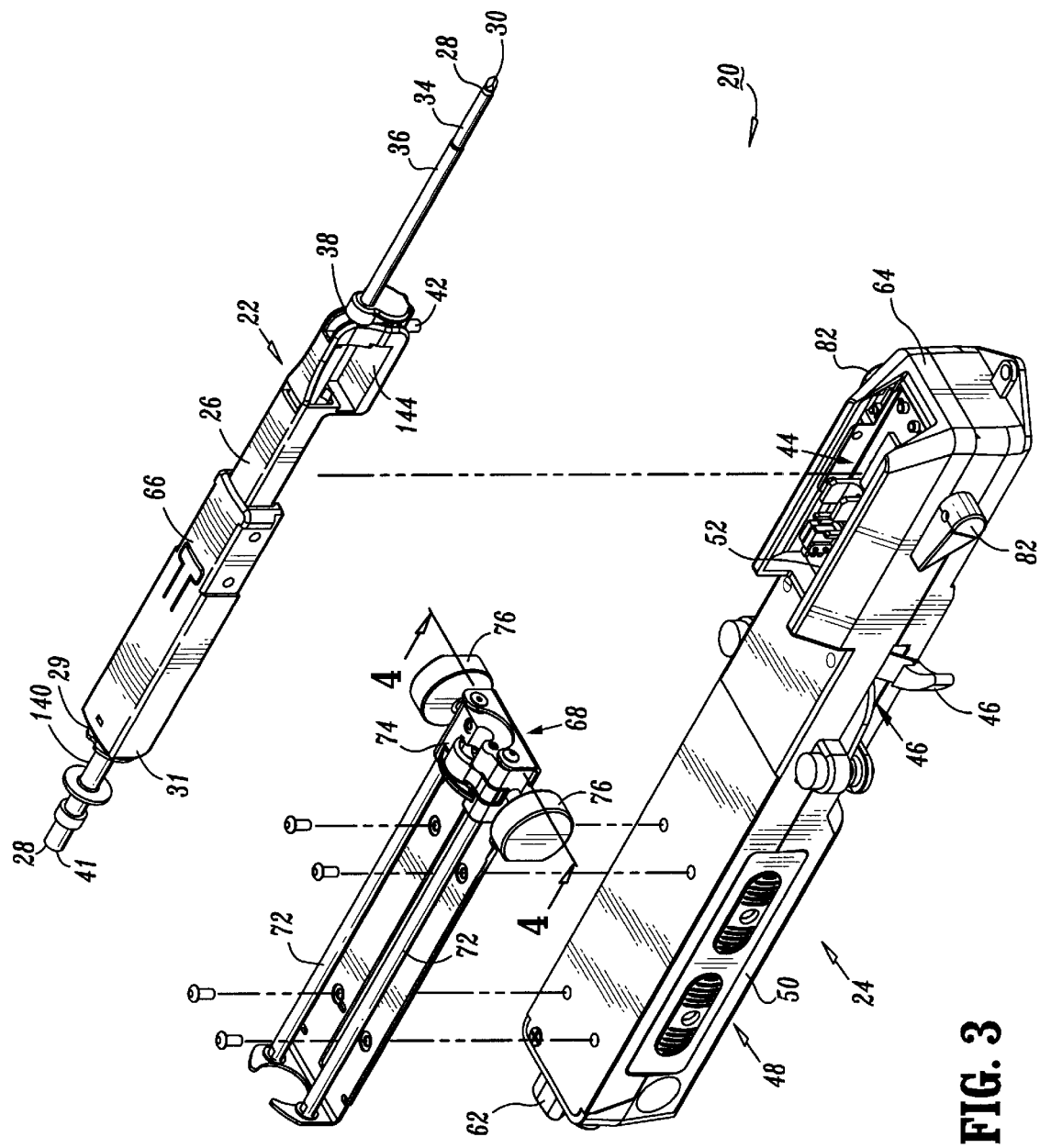
FIG. 3 is an exploded perspective view of the biopsy instrument driver apparatus embodiment of FIG. 1.

Referring to FIGS. 1–3, biopsy instrument 22 includes three main tubular components supported by a housing 26. Biopsy instrument 22 is, preferably, in the form of a disposable loading unit which is adapted for removable attachment to apparatus 24 (described hereinbelow). It is contemplated that biopsy instrument 22 may be of permanent fixture type. Biopsy instrument 22 includes an insertion end portion 27 configured and dimensioned for percutaneous introduction into a patient (not shown), for example, into the tissue of a compressed breast. Insertion end portion 27 extends from a distal end 38 of housing 26. A vacuum hub 29 is removably connected to a proximal end 31 of housing 26.

Figure 9:
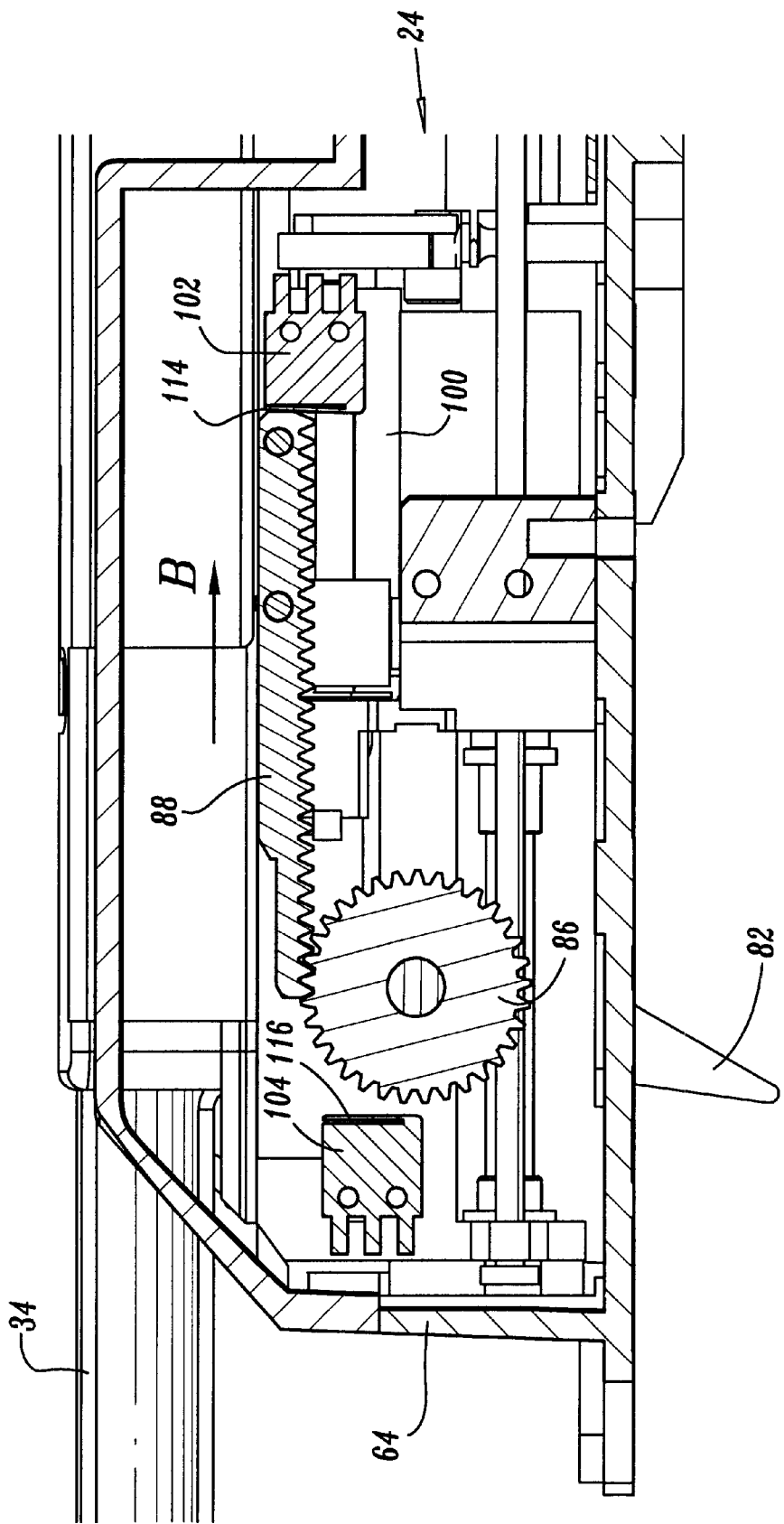
FIG. 9 is an enlarged side partial cross-sectional view which shows a cutting element controller assembly in a fully retracted position.

Biopsy instrument 22 includes a vacuum tube 28 having a sharpened distal penetrating end 30 and a tissue receiving portion, for example, tissue basket 32 (shown in FIG. 9) adjacent to distal penetrating end 30. Vacuum tube 28 is an innermost component of biopsy instrument 22 which is introduced into a target tissue mass 122 (shown in FIGS. 10 and 13) of a patient. Referring to FIGS. 1–3, the vacuum/controller module provides a vacuum source which interfaces with vacuum hub 29 through a first vacuum port 40 communicating suction to an area adjacent tissue basket 32 to draw at least a portion of target tissue mass 122 into tissue basket 32.

A tissue cutting element, for example knife tube 34 is rotatably disposed about vacuum tube 28. Knife tube 34 is configured to advance distally around the outside of vacuum tube 28 while rotating, in order to sever a target tissue portion 136 (shown in FIG. 13) from target tissue mass 122 (shown in FIGS. 10 and 13), as will be discussed hereinbelow. Once target tissue portion 136 is severed, vacuum tube 28 is retracted within knife tube 34 to remove the sample.

Biopsy instrument 22 also includes an outer tube 36 which is removably attached to distal end 38 of housing 26 for longitudinal sliding relative thereto. Outer tube 36 is, preferably, transparent to x-rays and maintains position of a portion of insertion end portion 27 inside targeted tissue mass 122, as biopsy instrument 22 and knife tube 34 are retracted to take an x-ray of the biopsy site.

A second vacuum port 42 is attached to distal end 38 of housing 26 of biopsy instrument 22 providing a second interface with the vacuum/control module. It is contemplated that apparatus 20 may interface with the vacuum/controller module at multiple ports. Second vacuum port 42 aspirates fluid from the biopsy site into a disposable canister provided on the vacuum/controller module(not shown). An example of a biopsy instrument similar to biopsy instrument 22 and a more detailed explanation of the components and method of operation are disclosed in pending application Ser. No. 09/040,244 entitled "Biopsy Apparatus and Method" to Farascioni et al. filed on Feb. 20, 1998, the entire contents of which are hereby incorporated by reference.

As shown in FIGS. 1–3 biopsy instrument 22 is mounted to drive apparatus 24. Drive apparatus 24 is configured and dimensioned for attachment to an instrument positioning stage of a stereotactic imaging apparatus (not shown). Examples of stereotactic imaging apparatus which are used to perform biopsy procedures are commercially available from LORAD Corporation of Danbury, Conn. or from Fischer Imaging Corporation of Denver, Colo. Alternatively, apparatus 24 may be adapted to fit on or interact with other suitable medical imaging apparatus.

In FIGS. 1–3, drive apparatus 24 includes a linear motion control mechanism such as knife driver subassembly 44, a piercing subassembly 46 which includes an insertion mechanism, an electrical subassembly 48 and a housing 50. Piercing subassembly 46 provides an operator of apparatus 20 with the ability to rapidly insert a portion of biopsy instrument 22 into a tissue mass as an alternative to manually translating biopsy instrument 22 into the tissue mass using the translation capabilities of a imaging apparatus.

Figure 5:
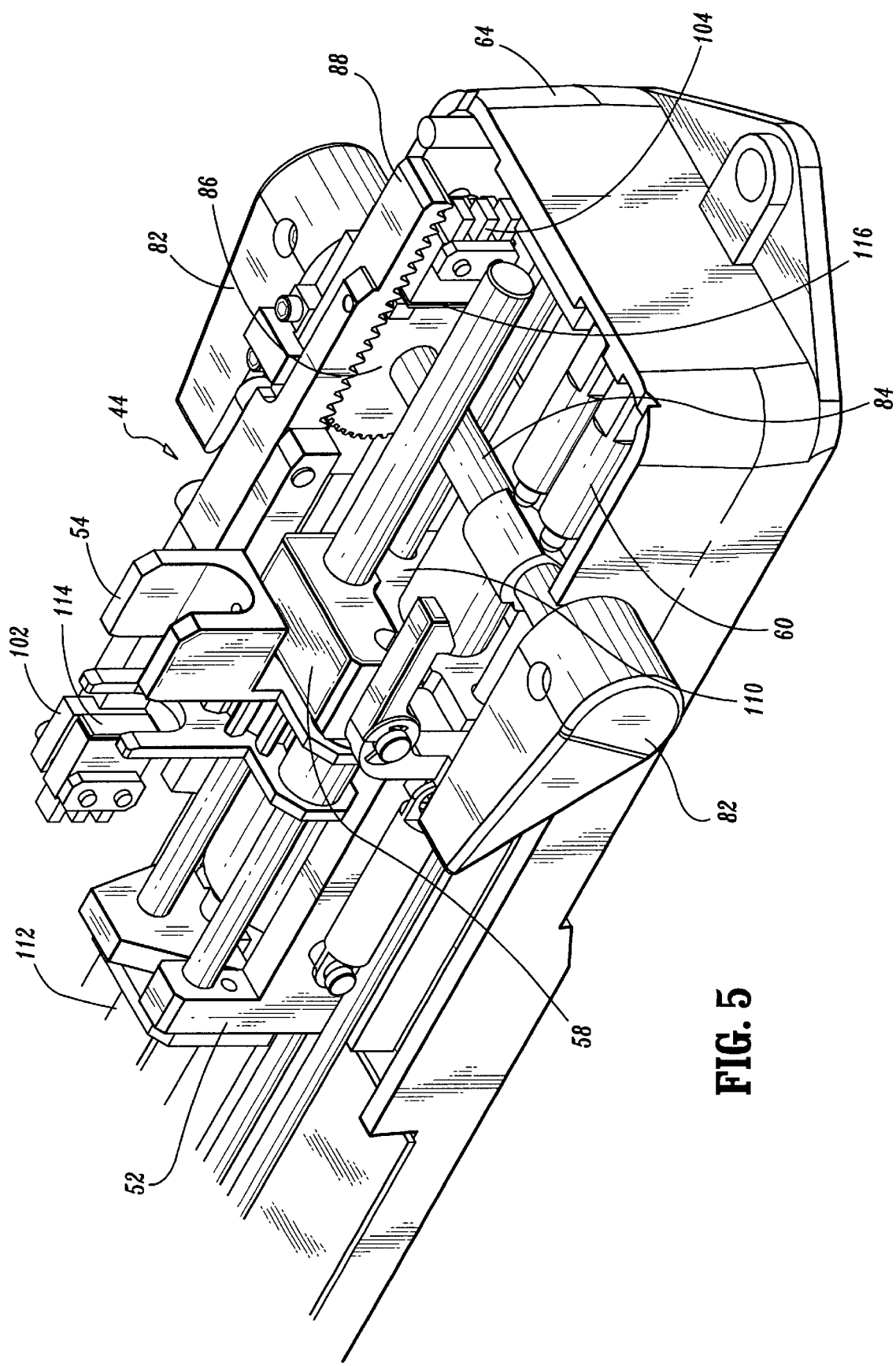
FIG. 5 is an enlarged perspective partial side view of a distal portion of a drive assembly of FIG. 1.
Figure 6:
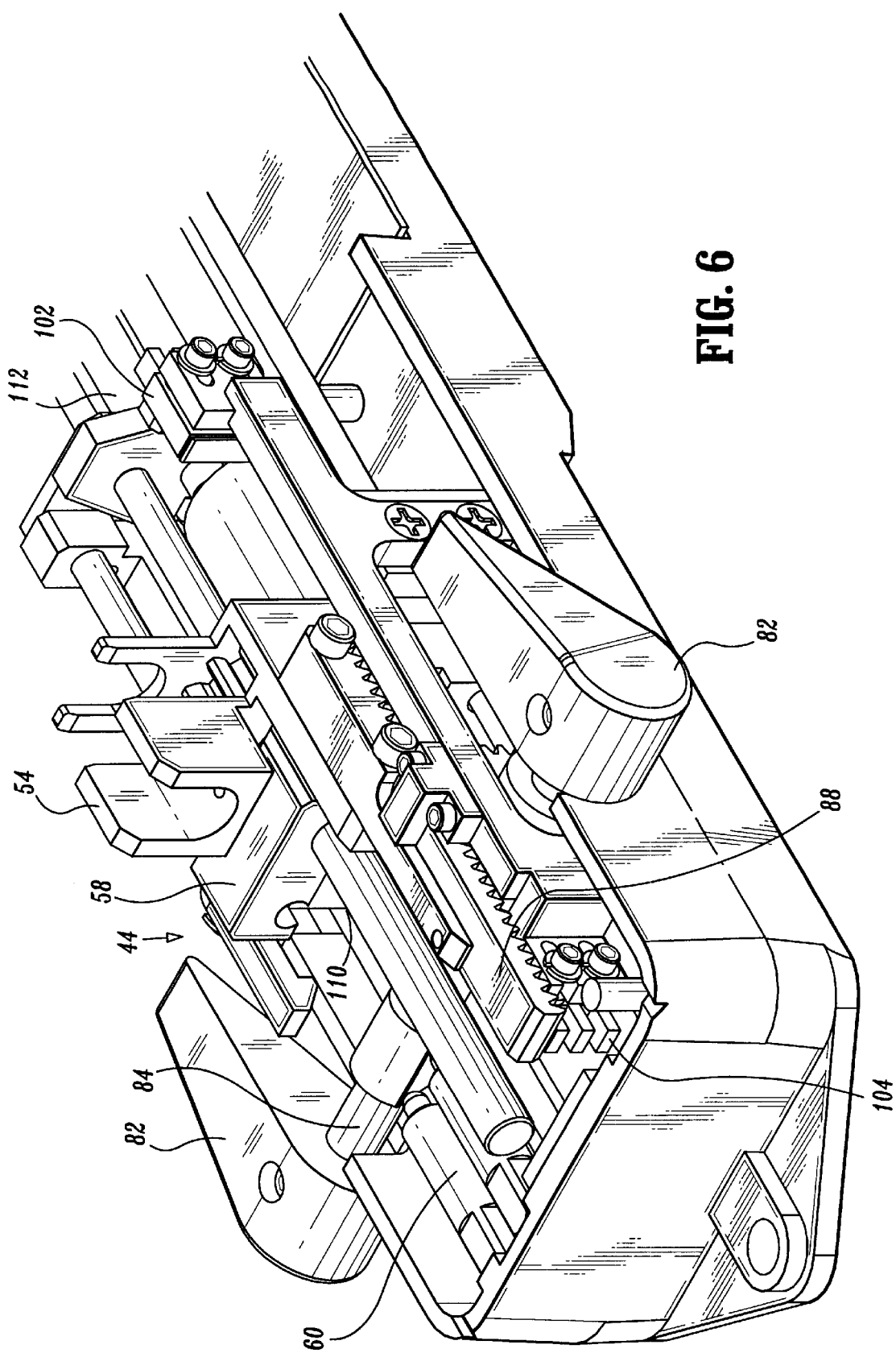
FIG. 6 is an enlarged perspective partial side view of a distal portion of the drive assembly showing the reverse angle of FIG. 5.

Referring to FIGS. 3, 5 and 6, piercing subassembly 46 includes a carriage such as sled 52 which supports biopsy instrument 22 and knife driver subassembly 44 such that upon firing of driver apparatus 24, sled 52 is thrust forward by releasing the stored energy of a spring. It is also contemplated that loaded 52 may be fired with other firing modalities such as, for example, pneumatic, hydraulic, etc.

Figure 10:
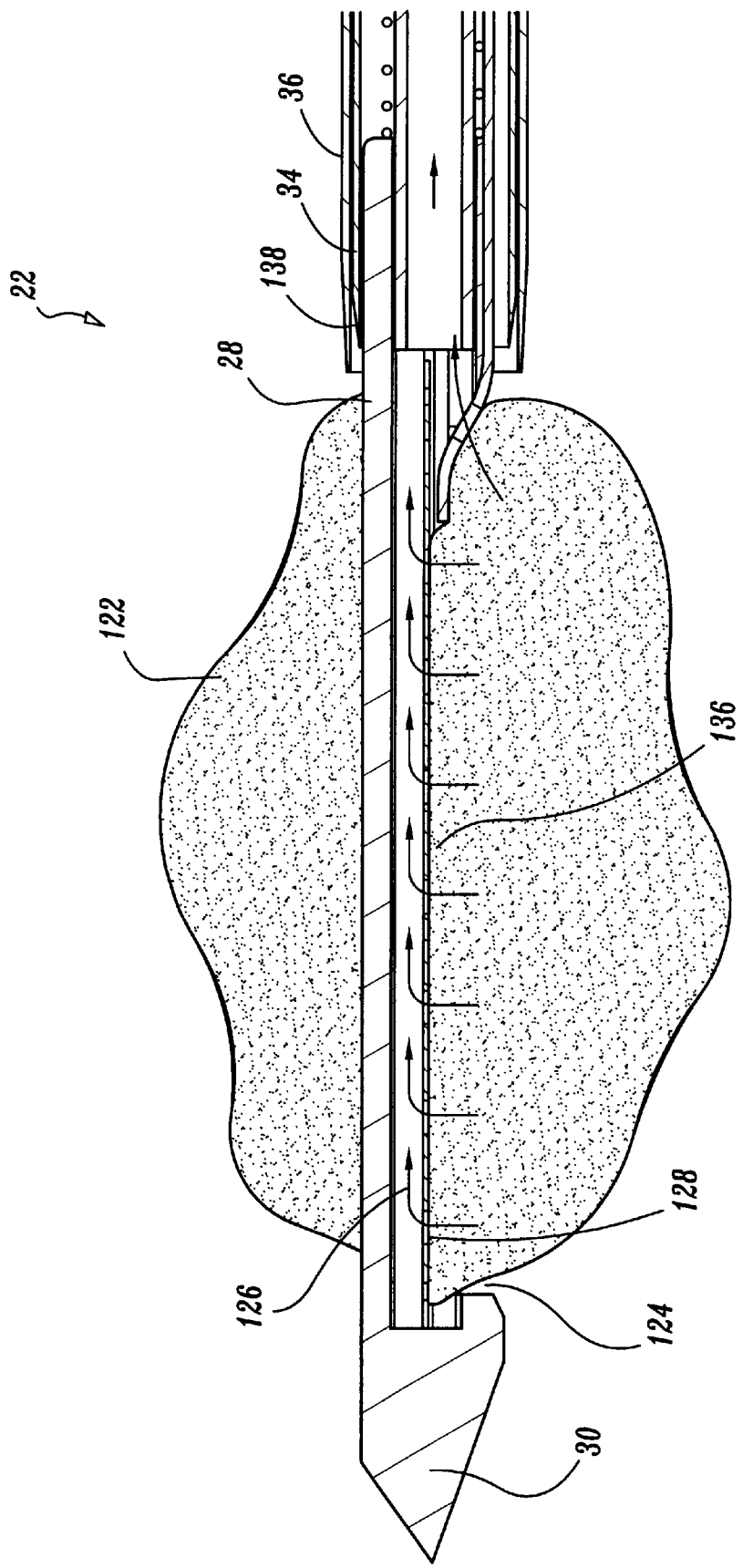
FIG. 10 is an enlarged cross-sectional view showing fluid flow lines of suction being applied and a tissue mass being drawn into a lateral tissue receiving opening formed in the biopsy apparatus.
Figure 13:
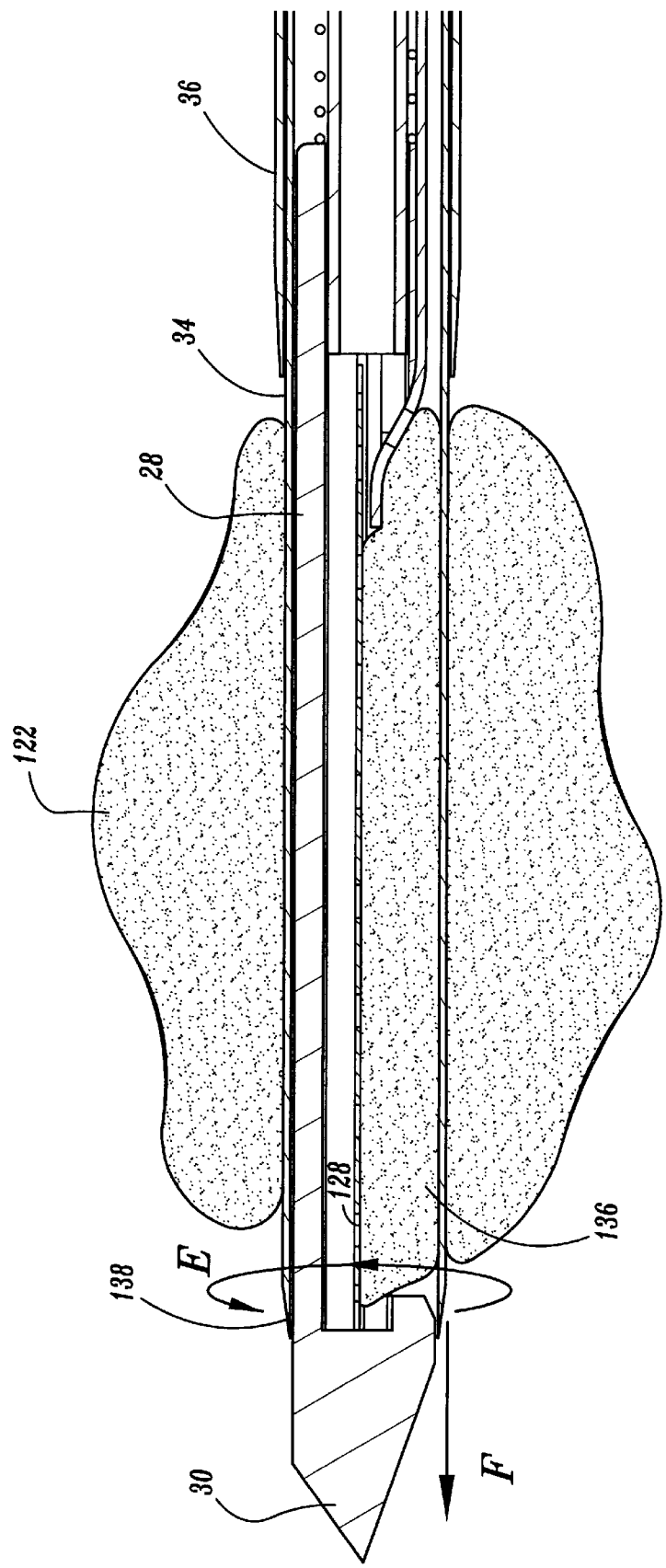
FIG. 13 is an enlarged cross-sectional view showing a knife tube being rotated and advanced distally to sever a tissue mass into the lateral opening in the biopsy apparatus shown in FIG. 1.

Upon firing of sled 52, biopsy instrument 22 is thrust forward so that biopsy instrument 22 pierces tissue for entry into a targeted tissue mass 122 (shown in FIGS. 10 and 13). Preferably, the minimum piercing force should be approximately 20 lbs., although greater forces are contemplated. Upon firing of driver apparatus 24, biopsy instrument 22 is, preferably, fired a distance of approximately 18–20 mm. It is contemplated that various amounts of force may be applied resulting in variable piercing distances for different degrees of penetration into a tissue mass depending on the biopsy application.

Referring to FIGS. 1–3, cocking arms 56 are provided, one on each side of drive apparatus 24 to facilitate cocking of piercing subassembly 46 from either side of housing 50, thereby permitting one handed operation. Cocking arms 56 are manually accessible by an operator to load a spring connected to sled 52 from a relaxed state. Once cocking arms 56 are cocked into place, a spring load is applied to the spring connected to sled 52. Upon release after loading the spring, cocking arms 56 then freely release and become disengaged with sled 52 and return to a relaxed state. Piercing subassembly 46 may then be fired to rapidly thrust biopsy instrument 22 into targeted tissue mass 122 (shown in FIGS. 10 and 13) so that sharpened distal penetrating end 30 of biopsy instrument 22 is injected into the target tissue or tissue immediately adjacent the target tissue depending on the user's preference.

A cocking position sensor 60 is also included that detects whether sled 52 in a cocked position thus disabling the cutting action of knife tube 34 during firing of driver apparatus 24. Cocking position sensor 60 preferably provides a signal that sled 52 is cocked which will result in deactivation of a motorized rotary driver of knife tube 34.

A user operated fire button 62 disposed on the rear surface of housing 50, releases sled 52 from the cocked position. Fire button 62 is also accessible from either side of housing 50 and permits one handed operation for firing of apparatus 20.

Sled 52, sled position sensor 60 are mounted to a base 64 of housing 50, as shown in FIGS. 1–3, 5 and 6. In FIGS. 1–3, a body portion 66 of biopsy instrument 22 is secured over sled 52 via a snap fit.

As shown in FIGS. 2 and 3, driver apparatus 24 includes a tissue retract mechanism 68. Tissue retract mechanism 68 interfaces with biopsy instrument 22 and drive apparatus 24. Tissue retract mechanism 68 is mounted to housing 50 of drive apparatus 24. A cover 70, as shown in FIGS. 1 and 2, covers tissue retract mechanism 68.

Figure 4:
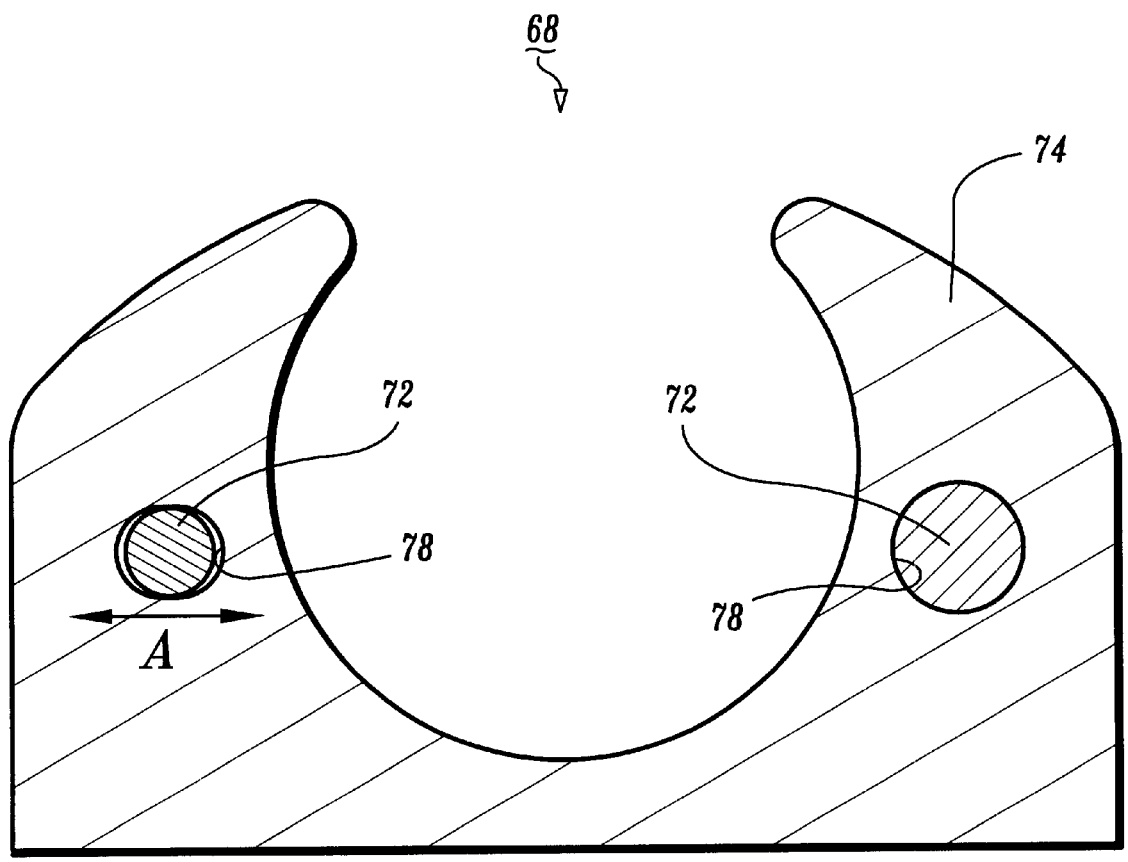
FIG. 4 is a cross-sectional view taken along section line 4—4 of FIG. 3.

Referring to FIGS. 2–4, tissue retract mechanism 68 includes a pair of longitudinal guide members, such as, rails 72 which are slidably supported by a pair of mounting flanges extending upwardly from a mounting bracket. A retention member such as slide block 74 supports proximal end of vacuum tube 28. A pair of indexing knobs 76 are provided, one on each side of slide block 74 to facilitate rotational orientation of tissue basket 32, i.e., the clock positioning. Slide block 74 is supported on rails 72 for slidable movement within the range of linear translation of a biopsy instrument 22. As shown in FIG. 4, slide block 74 defines a pair of bores 78 for slidably receiving rails 72. As shown by arrow A, at least one of rails 72 has a floating feature within bore 78. In particular, bore 78 is configured and dimensioned to provide a tolerance whereby at least one of rails 72 may freely move within the limits of bore 78. This floating feature allows slide block 74 to have a range of motion vertically during linear translation of biopsy instrument 22 to prevent binding of slide block 74 during such motion.

Figure 7:
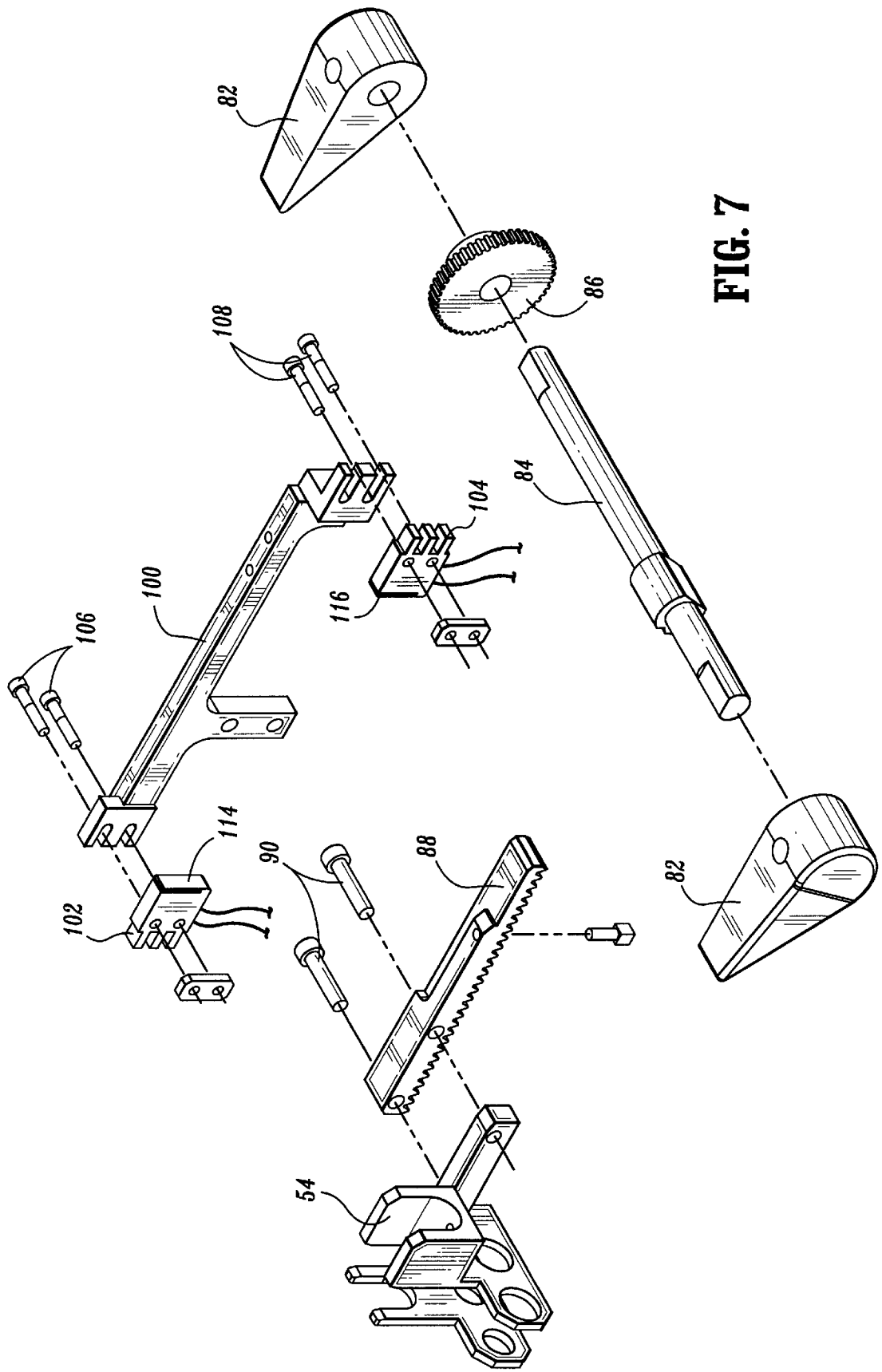
FIG. 7 is an exploded perspective view of some of the principal components of a cutting element control assembly of the biopsy instrument driver apparatus shown in FIG. 1.

As shown in FIGS. 5–7, driver apparatus 24 includes knife driver subassembly 44 which facilitates linear translation of knife tube 34 of biopsy instrument 22 via a manual operation. Knife driver subassembly 44 includes a motorized driver for rotating knife tube 34 for cutting tissue and provides feedback by way of microswitches that knife tube 34 is in a full forward position or in a fully retracted position. Knife driver subassembly 44 linearly translates knife tube 34 over tissue basket 32 of biopsy instrument 22.

Knife driver subassembly 44 is of a rack and pinion gear design and is manually manipulated via a pair of toggle knobs 82, one on each side of drive apparatus 24 and mountable within housing 50, while being accessible from both sides thereof permitting one handed operation. Toggle knobs 82 facilitate a range of linear travel of knife tube 34 between a full forward position wherein knife tube 34 completely covers tissue basket 32 but does not extend beyond sharpened distal penetrating end 30, and a fully retracted position whereby knife tube 34 completely exposes tissue basket 32.

As shown in FIG. 7, toggle knobs 82 are attached by a spindle shaft 84 which supports a pinion gear 86. Pinion gear 86 engages a rack 88. Rack 88 is attached to cradle 54. Pins 90 secure rack 88 to cradle 54 which supports knife tube 34 for linear translational movement. Knife driver subassembly 44 also includes arm 100 which supports a proximal microswitch 102 and a distal microswitch 104. Microswitches 102 and 104 are electrically connected to the drive motor and to the vacuum/controller module. Rack 88 linearly translates between proximal microswitch 102 and distal microswitch 104. Upon corresponding linear translation of knife tube 34, signals are transmitted on the status of knife tube 34 between a forward position and a retracted position. Proximal microswitch 102 is attached to arm 100 by pins 106 and distal microswitch 104 is attached to arm 100 by pins 108.

Referring to FIGS. 5 and 6, knife driver subassembly 44 includes a first position sensor 114 and a second position sensor 116. First position sensor 114 detects knife tube 34 in the fully retracted position exposing tissue basket 32. Second position sensor 116 detects knife tube 34 in the full forward position and covering the entire tissue basket 32, but not beyond sharpened distal penetrating end 30. A forward lock 110 is provided to lock knife tube 34 into its full forward position to ensure that a position sensor 114 remains activated when knife tube 34 is fully forward and to maintain position of knife tube 34 in targeted tissue mass 122, as vacuum tube 28 is retracted to unload a tissue sample from biopsy instrument 22. Forward lock 110 also maintains knife tube 34 in a full forward position when firing sled 52. A retracted lock 112, is provided to lock knife tube 34 into its fully retracted position so that second position sensor 114 remains activated when knife tube 34 is fully retracted.

Knife tube 34 rotates for cutting a tissue sample by a rotary drive motor of knife driver subassembly 44. The rotary drive motor actuates in response to signals received from first position sensor 114 and second position sensor 116. Biopsy instrument 22 is configured and dimensioned to interface with knife driver subassembly 44 by the meshing of a gear formed on knife tube 34 with a gear or gears which are operatively connected to the drive motor. The motor is mounted to knife driver subassembly 44 so that knife tube 34 can be linearly translated while being rotated. The above components of knife driver assembly 44 and the drive motor are mounted to base 64 of knife driver subassembly 44. First position sensor 114 and second position sensor 116 send signals to electrical subassembly 48, corresponding to the position of knife tube 34 within its linear translational range of motion between its forward position and retracted position. The drive motor then correspondingly receives start and stop actuation signals from electrical subassembly 48.

For biopsy instrument 22 to be properly loaded within drive apparatus 24, knife driver subassembly 44 must be in the full forward position for proper alignment with a rotary gear (not shown) of biopsy instrument 22 with the motor.

Driver apparatus 24 further includes electrical subassembly 48 which receives signals corresponding to the status of sled position sensor 60 of piercing subassembly 46 and first position sensor 114 and second position sensor 116 of knife driver subassembly 44. Upon receiving signals, electrical subassembly 48 transmits signals to a vacuum supply unit which may be in the form of a separate vacuum/controller module(not shown) corresponding to the status of the position sensors for actuation of the vacuum and the drive motor. Electrical subassembly 48 is mounted to base 64 and housed within housing 50.

In operation, biopsy instrument 22 is loaded onto driver apparatus 24. Knife driver subassembly 44 is manipulated to a full forward position, as shown by the position of rack 88 in FIGS. 11 and 12. Knife driver subassembly 44 is in the full forward position when rack 88 contacts distal microswitch 104. The full forward position aligns a knife tube gear of biopsy instrument 22 with a drive gear of driver apparatus 24 so that biopsy instrument 22 may snap fit into driver apparatus 24. Preferably, knife driver subassembly 44 is locked in the full forward position by forward lock 110 until biopsy instrument 22 is properly snap fit, which releases the lock.

Figure 8:
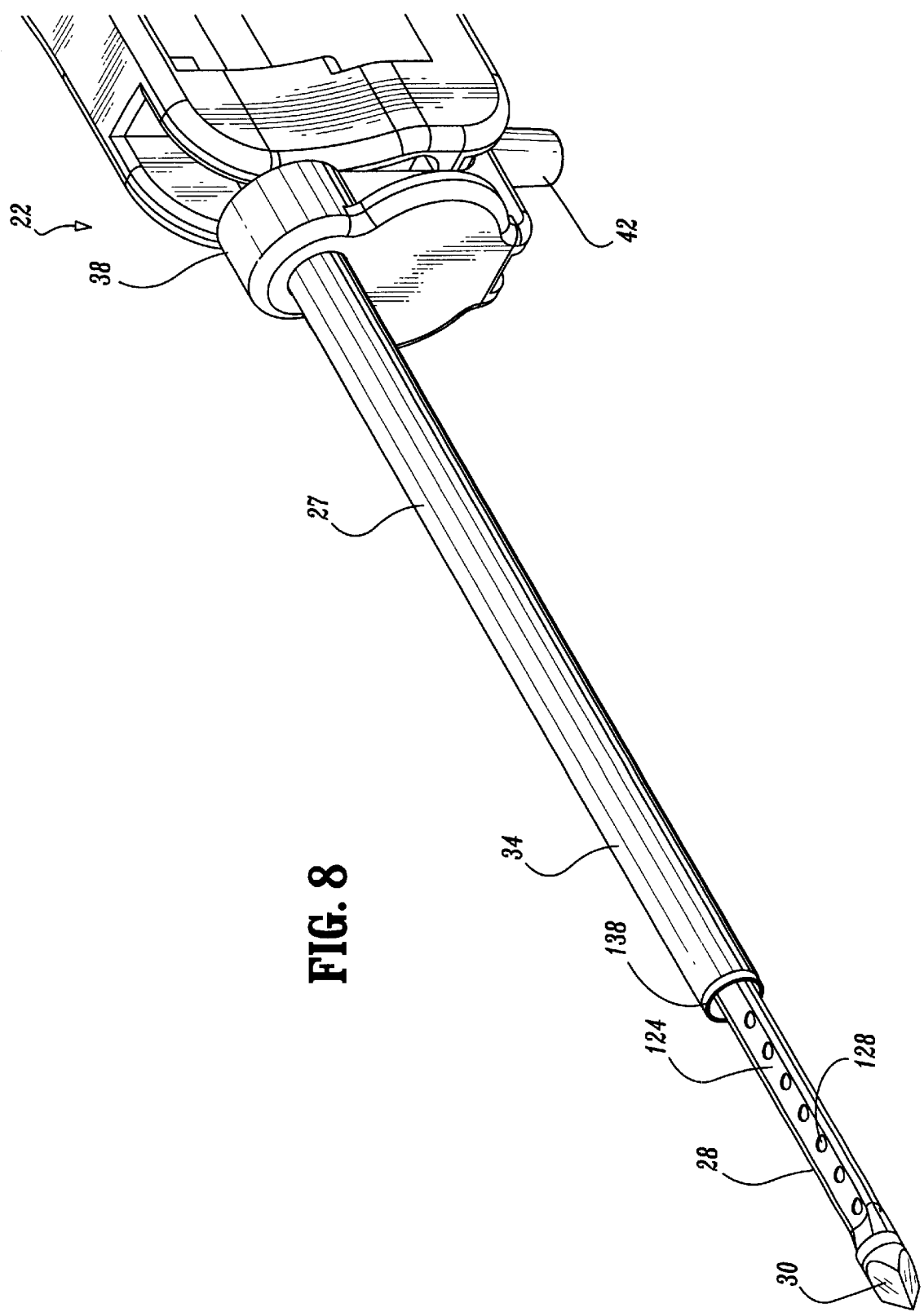
FIG. 8 is an enlarged perspective view of a distal portion of a biopsy instrument.

As shown in FIG. 8, sharpened distal penetrating end 30 of biopsy instrument 22 is moved into alignment with the coordinates of target tissue mass 122 by moving an imaging table (not shown) according to, e.g., a stereotactic image. A patient is positioned on the imaging table for a stereotactic image to determine the exact coordinates of target tissue mass 122 of the patient. Biopsy instrument 22 is advanced toward the patient so that tissue basket 32, which is covered by knife tube 34 during initial insertion into the patient, is inserted into the patient adjacent targeted tissue mass 122. Advancement of biopsy instrument 22 is accomplished by either manual translation capabilities of the imaging table or, preferably, by firing piercing subassembly 46 of drive apparatus 24, as previously described.

Specifically biopsy apparatus 22 is fired into targeted tissue mass 122 by manipulation of firing button 62. Knife tube 34 is maintained in the full forward position, thus sled position sensor 60 maintains deactivation of the knife rotary drive.

To obtain tissue sample 136, as shown in FIGS. 8–13, toggle knobs 82 are manipulated so that knife drive subassembly 44 and knife tube 34 are retracted to the fully retracted position, shown by arrow B. In the fully retracted position, rack 88 contacts proximal microswitch 102 actuating first position sensor 114. First position sensor 114 signals electrical subassembly 48 which in turn signals the vacuum/controller module activating the vacuum source in fluid communication with tissue basket 32.

Referring to FIGS. 8 and 10, applied suction draws a portion of targeted tissue mass 122 into tissue basket 32 through a lateral opening 124 of vacuum tube 28. Suction flow arrows 126 show the direction and location of the force exerted on target tissue mass 122. The suction force passes through the plurality of holes 128 in vacuum tube 28 to draw tissue sample 136 therein.

Figure 11:
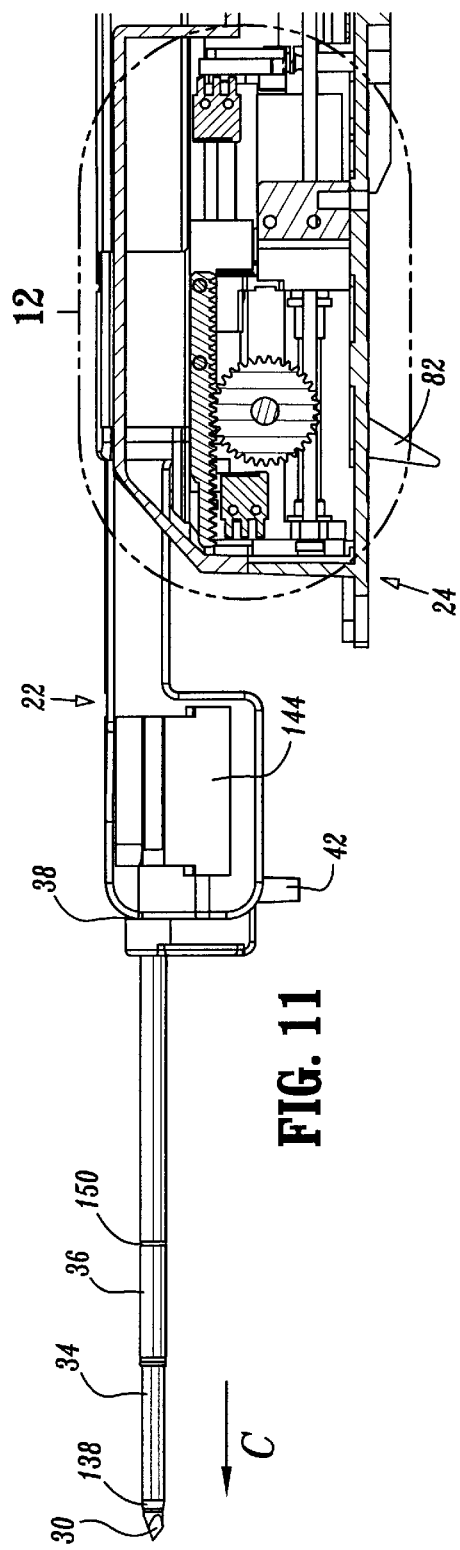
FIG. 11 is a side view in part cross-section of the distal portion of the biopsy instrument driver apparatus, showing the cutting element controller assembly in a fully forward position.
Figure 12:
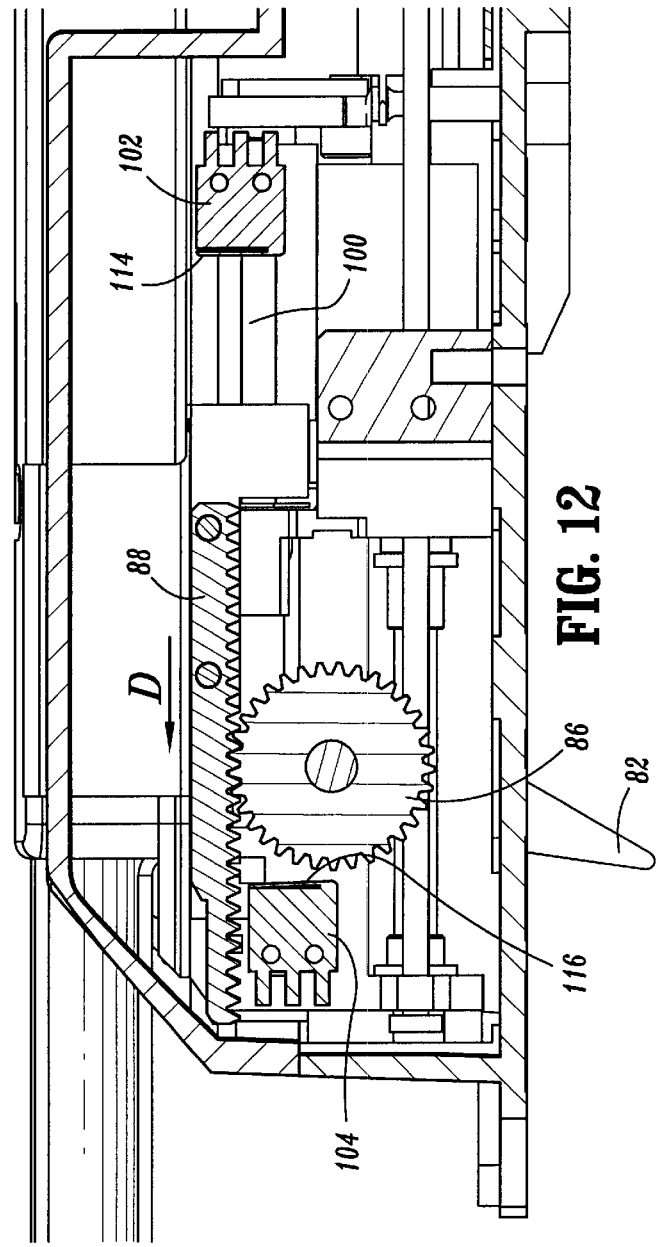
FIG. 12 is an enlarged cross-sectional-view of the indicated area of detail as shown in FIG. 11.

As shown in FIGS. 11–13 knife tube 34 and knife driver subassembly 44 are manually advanced distally by toggle knobs 82 to a full forward position. During this motion, rack 88 breaks contact with proximal microswitch 102 actuating first position sensor 114, signaling electrical subassembly 48, thereby activating the knife rotary driver to rotate knife tube 34. Preferably, the drive motor causes knife tube 34 to rotate at approximately 1200 to 1400 rpm. Rotating knife tube 34 may be further manually advanced over tissue basket 32 to sever targeted in tissue sample 136 held in receiving basket 32 by the vacuum source.

When tissue sample 136 is enclosed by knife tube 34 suction is no longer needed and may be removed. Once knife tube 34 completes its distal travel, rack 88 correspondingly contacts distal microswitch 104 actuating second position sensor 116. Second position sensor 116 signals electrical subassembly 48 which signals the rotary driver to slow rotation of knife tube 34 and signals the vacuum/controller module to shut off the vacuum supply. Upon actuation of second position sensor 116 and corresponding slow down of the rotary driver, the rotary driver is deactivated when tissue basket 32 is positioned at a predetermined orientation, for example, a three o'clock or nine o'clock position.

Once knife tube 34 is fully distally advanced, a locking wheel and indexer 140 (shown in FIG. 2) located on proximal end 31 of biopsy instrument 22 is rotated to a tissue eject position 144 until a lock tab 146 clears housing 26 of biopsy instrument 22. Vacuum tube 28 is thereby released and permits withdrawal of vacuum tube 28 and, therefore, tissue basket 32 from within knife tube 34. Once vacuum tube 28 is withdrawn such that tissue basket 32 is adjacent to a discharge opening 148 in knife tube 34, a tissue removal assist member (not shown) enters into tissue basket 32 such that an inwardly deflected portion of the tissue removal member contacts the proximal end of the severed tissue sample, thereby urging the tissue sample out of the tissue basket.

Upon completion of the desired amount of sampling, outer tube 36 is moved distally to a position a radiopaque marker 150 (FIG. 1) formed on outer tube 36 in relative alignment with the location of the biopsy site and length of the location where tissue basket 32 has previously aligned. Outer tube 36 may then be detached from biopsy instrument 22 and apparatus 20 translates away from targeted tissue mass 122 of a patient so that the tissue may be imaged without interference from the radiopaque nature of the remaining components of biopsy instrument 22.

Upon completion of the imaging, if it is determined that further sampling is desired or necessary, biopsy instrument 22 may be reinserted through outer tube 36 and reconnected with housing 26 of biopsy instrument 22. Additional sampling may then be taken as previously described above. Additionally, if desired, aspiration may be performed at the biopsy site if there is bleeding. An aspirator vacuum source is connected to vacuum port 42 (FIGS. 1 and 2) and aspiration may be performed with knife tube 34 in any position.

It will be understood that the various modifications may be made to the embodiments disclosed therein. Therefore, the above description should not be construed as limiting but merely as exemplifications of preferred embodiments. Those skilled in the art will envision other modifications within the scope and spirit of the claims appended hereto.

What is claimed is:

1. A driver apparatus for use with a biopsy instrument which includes a plurality of relatively movable elongated members, the driver apparatus comprising:

a housing;

an insertion mechanism including a carriage movably associated with the housing and being adapted to support the biopsy instrument to affect longitudinal movement of at least a portion of the biopsy instrument relative to the housing; and a linear motion control mechanism adapted to move a tissue cutting element of the biopsy instrument from a first position to a second position relative to a tissue receiving portion of the biopsy instrument wherein the tissue cutting element cuts tissue extending into a tissue receiving portion of the biopsy instrument; and a tissue retract mechanism which facilitates removal of a tissue specimen from the biopsy instrument without removing the entire biopsy instrument from a surgical site, the tissue retract mechanism including a retention member adapted to retain a portion of the biopsy instrument, the tissue retract mechanism further including a longitudinal guide member which slidably guides the retention member and is disposed relative to the housing in a manner to permit movement of the longitudinal side member relative to the housing.

2. A driver apparatus for use with a biopsy instrument which includes a tissue receiving portion and a cutting element, the driver apparatus comprising:

a housing;

an insertion mechanism adapted to support a biopsy instrument thereon, the insertion mechanism including a carriage movably associated with the housing such that the carriage is movable from a retracted position to an advanced position to affect longitudinal movement of the biopsy instrument; and a cutting element controller assembly operatively disposed on the housing, the controller assembly including:

a linear motion control mechanism adapted to move a tissue cutting element of the biopsy instrument from a first position to a second position relative to a tissue receiving portion of the biopsy instrument wherein the tissue cutting element cuts tissue extending into a tissue receiving portion of the biopsy instrument; and a motor operatively associated with the cutting element when the biopsy instrument is mounted on the biopsy instrument driver apparatus, such that the motor facilitates movement of the cutting element relative to the tissue receiving portion; and an enabling switch disposed relative to the linear motion control member and electrically connected to the motor such that movement of the linear motion control member from the second position to the first position, causes the switch to activate the motor.

3. A driver apparatus as recited in claim 1, wherein the tissue receiving portion of the biopsy instrument is in communication with a vacuum source.

4. A driver apparatus as recited in claim 1, wherein the biopsy instrument includes a sharpened distal penetrating end disposed adjacent the tissue receiving portion.

5. A driver apparatus as recited in claim 2, wherein the linear motion control mechanism includes a rack and pinion gear arrangement operatively connected to the tissue cutting element, the rack and pinion gear arrangement being manipulable to facilitate a range of longitudinal movement of the tissue cutting element between the first position, whereby the tissue cutting element encloses substantially all of the tissue receiving portion, and the second position, whereby the tissue cutting element exposes substantially all of the tissue receiving portion.

6. A driver apparatus as recited in claim 5, wherein the rack linearly translates between a proximal microswitch and a distal microswitch of the enabling switch, wherein contact with one of the proximal microswitch or the distal microswitch activates the motor.

7. A driver apparatus as recited in claim 6, wherein a first position sensor is disposed with the proximal microswitch and a second position sensor is disposed with the distal microswitch, the first position sensor detecting the tissue cutting element in the second position and the second position sensor detecting the tissue cutting element in the first position for activating and deactivating the motor.

8. A driver apparatus as recited in claim 2, further including a forward lock for maintaining the tissue cutting element in the first position.

9. A driver apparatus as recited in claim 2, further including a retracted lock for maintaining the tissue cutting element in the second position.

* * * * *